United States Patent [19]

Johnson et al.

[11] Patent Number: 5,025,809

[45] Date of Patent: Jun. 25, 1991

[54] RECORDING, DIGITAL STETHOSCOPE FOR IDENTIFYING PCG SIGNATURES

[75] Inventors: Keith H. Johnson; David A. Underwood, both of Houston, Tex.

[73] Assignee: Cardionics, Inc., Houston, Tex.

[21] Appl. No.: 442,143

[22] Filed: Nov. 28, 1989

[51] Int. Cl.⁵ .................................. A61B 7/02
[52] U.S. Cl. .............................. 128/715; 128/773
[58] Field of Search ............ 128/715, 773, 670, 700

[56] References Cited

U.S. PATENT DOCUMENTS

| | | | |
|---|---|---|---|
| Re. 29,921 | 2/1979 | Cherry et al. | 364/900 |
| 3,799,147 | 3/1974 | Adolph et al. | 128/715 |
| 3,921,624 | 11/1975 | Vogelman | 128/2.06 F |
| 4,115,864 | 9/1978 | Vick et al. | 364/550 |
| 4,301,809 | 11/1981 | Pinchak | 128/715 |
| 4,331,159 | 5/1982 | Bax et al. | 128/710 |
| 4,362,164 | 12/1982 | Little et al. | 128/715 |
| 4,417,306 | 11/1983 | Citron et al. | 364/415 |
| 4,483,346 | 11/1984 | Slavin | 128/710 |
| 4,519,398 | 5/1985 | Lisiecki et al. | 128/710 |
| 4,596,256 | 6/1986 | Ascher et al. | 128/710 |
| 4,617,938 | 10/1986 | Shimoni et al. | 1128/708 |
| 4,624,263 | 11/1986 | Slavin | 128/710 |
| 4,628,327 | 12/1986 | Anderson et al. | 128/710 |
| 4,770,189 | 9/1988 | Shyu | 128/773 |
| 4,779,199 | 10/1988 | Yoneda et al. | 364/413.03 |

*Primary Examiner*—William E. Kamm
*Assistant Examiner*—Scott M. Getzow

*Attorney, Agent, or Firm*—Browning, Bushman, Anderson & Brookhart

[57] ABSTRACT

The present invention is directed to a method for identifying characteristic phonocardiographic heart sounds using a novel, recording, digital stethoscope. The stethoscope comprises in combination the features of a standard air column stethoscope together with the features of a recording, digital stethoscope. Further, the stethoscope includes features permitting the detection and recording of at least a portion of the electrocardiographic wave pattern to aid in analysis of the phonocardiographic sounds. The system for identifying phonocardiographic sounds includes the described recording, digital stethoscope together with a computer and display device for storing, analyzing and displaying the detected sounds together with comparative sounds selected from a reference library. The method for identifying characteristic phonocardiographic sounds includes detecting the phonocardiographic sounds and at least a portion of the electrocardiographic wave pattern of the patient, digitalizing the detected signals, storing those signals, digitalizing the detected signals, storing those signals, analyzing those signals to produce a phonocardiographic signature, comparing that signature with reference PCG signatures and displaying visually and/or audibly the patient's phonocardiographic sounds together with the phonocardiographic sounds corresponding to the reference PCG signatures determined to be closest to the PCG signature of the patient.

21 Claims, 7 Drawing Sheets

RECORDING, DIGITAL STETHOSCOPE FOR IDENTIFYING PCG SIGNATURES

BACKGROUND OF THE INVENTION

1. Field of the Invention

The present invention generally relates to apparatus and methods useful in detecting, recording, analyzing and displaying phonocardiographic sounds. The present invention is particularly directed to a recording, digital stethoscope for detecting both phonocardiographic sounds and electrocardiographic wave patterns and for digitalizing and storing those signals. More particularly, the present invention further includes computer and display features for analyzing the digitalized signals to produce a characteristic phonocardiographic signature for the patient, for comparing that signature with stored reference signatures to select the most similar reference signatures and for displaying both audibly and visually the phonocardiographic sounds which produced one or more of the selected reference signatures and the signature produced for the patient.

2. Description of the Background

The heart and body produce hundreds of specific sounds, including heart, lung, bowel, circulatory and Korotkoff sounds. These sounds and combinations thereof are indicative of normal and abnormal conditions. Knowledge of these sounds provides valuable diagnostic information to the physician. The art of listening to these sounds and using them as diagnostic aids is known as auscultation. The ancients listened to these sounds by placing the ear to the chest or back of the patient. Later, the air column stethoscope was developed. The stethoscope has proven to be a valuable instrument for the transmission of these sounds to the examining physician. The air column stethoscope has remained relatively unchanged for more than a century. Recently, electronic stethoscopes using a transducer and appropriate electronics to detect the sounds have been developed.

The heart produces an electrical wave pattern and many complex sounds which can provide much valuable diagnostic information. However, the average physician typically has difficulty in interpretation of the highly complex sounds and combinations of sounds produced by the heart. Physicians especially trained to interpret these electrical patterns and sounds are known as cardiologists. Because a cardiologist often is not available, much of the information contained in these electrical patterns and sounds may be lost. Accordingly, it is desirable to provide an apparatus and method for recording these sounds to permit later analysis by a cardiologist. In an effort to address this problem, several recent patents have disclosed apparatus for recording the electrocardiographic wave patterns while others have disclosed apparatus for recording the phonocardiographic sounds. Even more desirable would be an apparatus and method which, in addition to such recording, would provide the average physician with assistance in making diagnoses based upon these sounds.

The standard air column stethoscope used by the medical profession employs a listening cup placed on the chest or back of the patient with the sound amplified by a simple bell and diaphragm into a standing air column terminating in earpieces for the physician's ears. The conventional stethoscope has remained relatively unchanged since the last century. Electronic stethoscopes have also been available for some time. In an electronic stethoscope the heart sounds are detected by a transducer and are electronically processed. The electronically processed signals are then employed to drive a speaker providing sound to an individual listener or to a group. Such devices permit amplification of the detected sounds. Recently recording capability, first analog and later digital, has been added to the electronic stethoscope. However, due to various problems, including excessive noise, electronic stethoscopes have not become popular.

Many problems exist with the use of conventional stethoscopes. In general, conventional stethoscopes offer very subjective information. For example, the hearing acuity of the user has significant bearing on the sounds observed. When a loud sound is followed by a soft sound, difficulty exists in detecting and assessing the intensity of the soft sound. This acoustical phenomenon is known as masking. It is difficult to time an abnormal heart sound with respect to the phase of the heart beat, an important aspect of murmur diagnosis. A fast heart rate can make both the recognition and timing of abnormal sounds difficult. This problem is often found with children and animals where heart rates are often much higher than in adult humans. External noise may often mask heart, lung, circulatory and Korotkoff sounds detected under non-ideal listening conditions. These and many other problems plague the conventional stethoscope.

Many of these subjective factors may be removed by visual display of the heart sounds. Most efforts at visual display of heart data have been directed to the electrocardiographic wave pattern. Because the electrocardiographic wave pattern, i.e., the electrical wave pattern generated by the heart, is more easily processed and displayed, the electronic monitoring, displaying and storing of the electrocardiographic wave pattern was addressed first. Many patents deal with the detection, storage and display of the electrocardiographic wave pattern.

Early efforts to visually display heart data were disclosed by Vogelman in U.S. Pat. No. 3,921,624. Bax in U.S. Pat. No. 4,331,159 disclosed the acquisition and visual display of analog electrocardiographic wave patterns on a helical track about a rotating cylinder. Shimoni in U.S. Pat. No. 4,617,938 and Citron in U.S. Pat. No. 4,417,306 disclosed systems for acquiring and recording electrocardiographic wave patterns. Both Bax and Shimoni disclosed the identification of the R-wave, that marker of the wave pattern separating the systolic and diastolic portions of the heart beat. Both Ascher in U.S. Pat. No. 4,596,256 and Lisiecki in U.S. Pat. No. 4,519,398 disclosed portable electrocardiographic wave recorders. Further, Lisiecki disclosed a transfer of the recorded signals to a fixed computer for visual display. Anderson in U.S. Pat. No. 4,628,327 disclosed the acquisition, digitalization and storage of electrocardiographic wave patterns in a circular memory. Upon tripping of an alarm indicating a preset abnormal condition, the attached recorder rapidly produces a visual output of the stored data both before and after the event which tripped the alarm. Yoneda in U.S. Pat. No. 4,779,199 similarly disclosed acquisition and digitalization of the electrocardiographic wave pattern. Further, U.S. Pat. No. 4,115,864 and U.S. Pat. No. R 29,921 both disclosed the acquisition and storage of electrocardiographic wave pattern data followed by a display of that data with previously recorded electrocardiographic wave patterns to permit a visual comparison of the results by the physician.

As the above patents illustrate, most efforts at electronic storage and display of heart data have been directed to the electrocardiographic wave pattern. This is because the ECG wave pattern is much simpler and at a significantly lower frequency than the phonocardiographic heart sounds. Detection, digitalization, storage and display of the phonocardiographic heart sounds are complicated by the presence of many other body sounds and by their higher frequency and more variable wave pattern. However, some work has been done in this area. Slavin in U.S. Pat. No. 4,483,346 disclosed a portable device for recording both an electrocardiographic wave pattern and phonocardiographic sounds. The phonocardiographic sounds were digitalized and stored for later transmission through a modem to a computer for storage and display. In U.S. Pat. No. 4,624,263, Slavin added cassette storage capability to the previously disclosed portable recorder. Further, Slavin disclosed the storage of abnormal phonocardiographic information for displaying with the patient's heart sounds to illustrate differences.

There has been a long felt but unfulfilled need within the medical profession for a device capable of aiding the non-specialist physician without access to a cardiologist for analyzing heart sounds. The present invention provides such an apparatus and method. Although the above patents disclose systems for detecting, storing and displaying the electrocardiographic wave pattern and, in the Slavin patents, the phonocardiographic heart sounds, none of these patents disclose a stethoscope capable of detecting and recording simultaneously both the phonocardiographic heart sounds and the electrocardiographic wave pattern while also providing a conventional air column listening device. None of the above patents discloses a system for analyzing the complex, phonocardiographic heart sounds to identify a plurality of characteristic features to produce a phonocardiographic signature for the patient. Further, none of the above patents discloses a system for comparing a patient's phonocardiographic signature with PCG signatures for a variety of normal and abnormal heart sounds maintained in a reference library to aid the physician in diagnosis. Finally, none of the above patents discloses a system for displaying one or more reference sounds selected after comparison of the phonocardiographic signatures.

SUMMARY OF THE INVENTION

The present invention provides a new and improved recording, digital stethoscope for use in a novel system and method for identifying phonocardiographic sounds by producing a phonocardiographic signature and comparing that signature to known phonocardiographic signatures in a reference library.

The system for identifying phonocardiographic sounds comprises a recording, digital stethoscope capable of detecting and recording both phonocardiographic (PCG) sounds and at least a portion of the electrocardiographic (ECG) wave pattern of the patent. The electrocardiographic wave pattern must include both the systolic and diastolic portions of the heart beat. The detected PCG and ECG signals are digitalized for storage. The system includes a computer and means for transmitting the recorded signals to the computer. The computer provides both memory and analysis functions. In the computer, the digital phonocardiographic sounds are analyzed to produce a phonocardiographic signature for the patient.

The phonocardiographic signature includes a systolic PCG signature, a diastolic PCG signature, the heart rate, and the location of the stethoscope where the PCG sounds were recorded. Both the systolic and diastolic PCG signatures include the type and timing of each short heart sound and the pitch, type and timing of each long heart sound. The signatures are derived by using the ECG wave pattern to divide the phonocardiographic heart sounds into systolic and diastolic phases. Each such phase is further subdivided into at least two and preferably four subphases. Each sound in the PCG measurement is then identified as either a short or long sound by determining whether the sound appears in one or more adjacent subphases. Each such sound is then identified by the phase and subphase in which it appears and by its timing with reference to the R-wave. Each short heart sound is identified by the phase and subphase in which it appears, together with its pitch, shape and timing with reference to the R-wave.

In the above manner a characteristic phonocardiographic signature is obtained for the patient. This signature is then compared in the computer with signatures stored in the computer in a library of reference PCG signatures. From this comparison one or more reference PCG signatures is selected as being the most similar to the patient's PCG signature. Finally, the system includes means for displaying, visually and/or audibly, the phonocardiographic heart sounds from which the patient's PCG signature and the selected reference PCG signatures were produced.

The system of the present invention employs a new, recording, digital stethoscope comprising means for detecting, digitalizing and recording both phonocardiographic heart sounds and the electrocardiographic wave pattern of the patient. Only that portion of the electrocardiographic wave pattern which is necessary to determine the systolic and diastolic portions of the heart beat need be detected and recorded. Preferably this is accomplished by detecting the R-wave with three electrodes symmetrically disposed about the periphery of the stethoscope cup. In a preferred embodiment this recording, digital stethoscope further comprises means for conveying the detected phonocardiographic sounds to the ears of the user of the stethoscope, most preferably a standing air column between the stethoscope cup and conventional ear pieces.

The apparatus and method of the present invention provide a means for detecting and identifying characteristic phonocardiographic patient sounds. The recording, digital stethoscope of the present invention, providing means for detecting and recording both the phonocardiographic heart sounds and the electrocardiographic wave pattern, provides the signals necessary to accomplish the desired goal. The present invention provides a system and method for aiding the non-specialist physician in diagnosing phonocardiographic heart sounds where access to a consulting cardiologist is unavailable or inconvenient. Further, the present invention provides a system and method for preserving such information for later analysis by a cardiology specialist. These and other meritorious features and advantages of the present invention will be more fully appreciated from the following detailed description and claims.

BRIEF DESCRIPTION OF THE DRAWINGS

Other features and intended advantages of the present invention will be more readily apparent from the references to the following detailed description in connection with the accompanying drawings, wherein.

While the invention will be described in connection with the presently preferred embodiment, it will be understood that it is not intended to limit the invention to this embodiment. On the contrary, it is intended to cover all alternatives, modifications and equivalents as may be included in the spirit of the invention as defined in the appended claims.

DETAILED DESCRIPTION OF THE PREFERRED EMBODIMENT

The present invention is directed to a method and apparatus for identifying characteristic phonocardiographic heart sounds. These sounds are identified by detecting, digitalizing, storing and analyzing the patient's phonocardiographic heart sounds together with at least a portion of the simultaneous electrocardiographic wave pattern of the patient.

The patient's digitalized phonocardiographic heart sounds are analyzed in a computer to obtain the patient's phonocardiographic signature. The sounds occurring in both the systolic and diastolic portions of the heart beat are analyzed and identified as either short duration heart sounds or long duration heart sounds. This identification is accomplished by further subdividing each of the systolic and diastolic phases into at least two and preferably four subphases. A short sound is a sound which occurs in only one subphase. Short sounds include the first and second heart sounds and the splitting of these sounds, the third and fourth heart sounds, clicks and ejection sounds. A long duration heart sound is one that appears in more than one adjacent subphase. Long sounds are generally known as murmurs. The method provides for the identification of each heart sound in the patient's phonocardiogram by reference to the phase and subphase in which the sound appears together with its timing in reference to the R-wave of the patient's electrocardiographic wave pattern. Both short and long duration heart sounds are so identified. Long duration heart sounds are further identified by their pitch and shape.

The patient's phonocardiographic signature for the patient comprises both a systolic PCG signature and diastolic PCG signature wherein each heart sound has been identified as above, together with the patient's heart rate and the location of the stethoscope when the PCG sounds were recorded.

In a further aspect of the present invention, the patient's PCG signature is compared with the PCG signatures stored in a reference library in the computer to obtain one or more reference PCG signature determined to be the closest to the patient's PCG signature. After this determination, the phonocardiographic heart sounds of one or more of the selected reference PCG signatures may be displayed visually and/or audibly. This display may be either alone or in close proximity to the patient's heart sounds. Visual display permits the physician to make a further visual comparison of both the reference and patient heart sounds before final diagnosis. Audible display permits the physician to listen to the patient's heart sound alternately with one or more of the selected reference heart sounds before final diagnosis.

Figure 1:
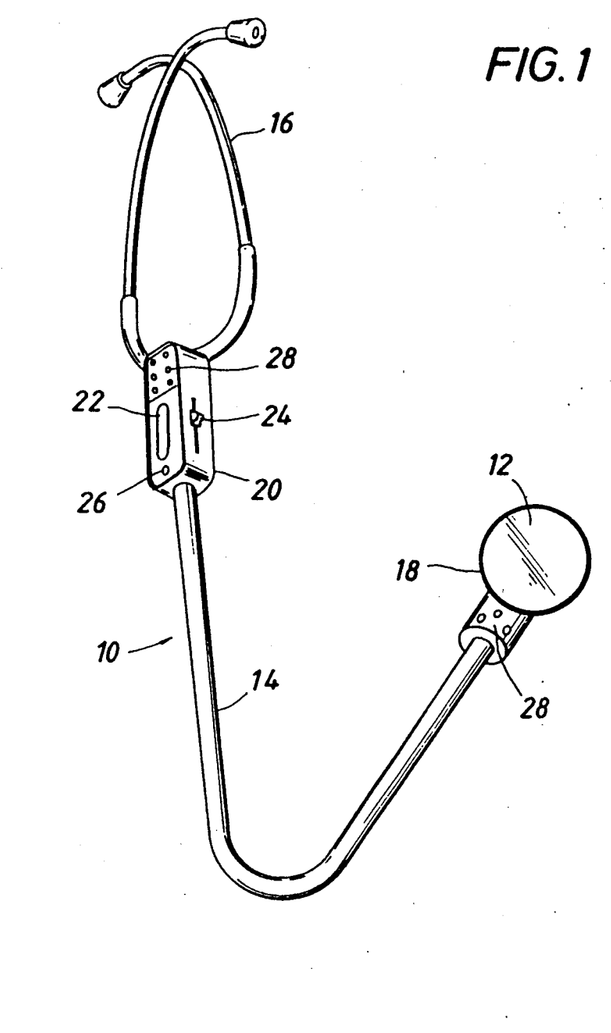
FIG. 1 is an illustration of a recording, digital stethoscope in accord with the present invention.

A recording, digital stethoscope in accord with the present invention is illustrated in FIG. 1. The apparatus of the present invention includes a recording, digital stethoscope 10 for detecting, digitalizing and recording both the phonocardiographic heart sounds and the electrocardiographic wave pattern of a patient. Further, in a preferred embodiment, the stethoscope 10 includes means for directly conveying the detected heart sounds to the ears of the physician. Preferably this means is a standing air column. The stethoscope 10 includes a stethoscope cup 12 for placement on the body of the patient for detecting heart sounds. A conventional bell stethoscope cup and diaphragm is preferred. About the periphery of stethoscope cup 12 are disposed at least three electrodes 18 for detecting at least a portion of the electrocardiographic wave pattern of the patient. Preferably three electrodes are symmetrically disposed for detecting the R-wave to permit identification of the systolic and diastolic portions of the heart beat. Cup 12 is attached to flexible tubular member 14. Tubular member 14 provides an internal conduit for a conventional standing air column together with a housing for necessary electrical wiring. Tubular member 14 is attached at its upper end to housing 20 wherein are disposed the electronic components of the stethoscope used for digitalizing and temporarily storing the detected PCG and ECG signals. Further, at its upper end, tubular member 14 and the standing air column therein are connected to conventional ear pieces 16 for listening by the physician. Housing 20 further includes volume control 24 attached to a variable analog amplifier (not shown) for controlling the volume of the signals delivered to earpieces 16 through the standing air column in tubular member 14. Also disposed in housing 20 is a speaker 22 through which the digitalized PCG signals may be replayed. Disposed on one or both of cup 12 and housing 20 are a plurality of controls 28 providing means for actuating and controlling the digital stethoscope. Controls 28 provide means for actuating the digital acquisition of sounds, the labeling of data, and the recording/playback of phonocardiographic data. Plug 26 in housing 20 provides means for transmitting recorded data from and instructions to stethoscope 10 through appropriate electrical lines (not shown).

Figure 2:
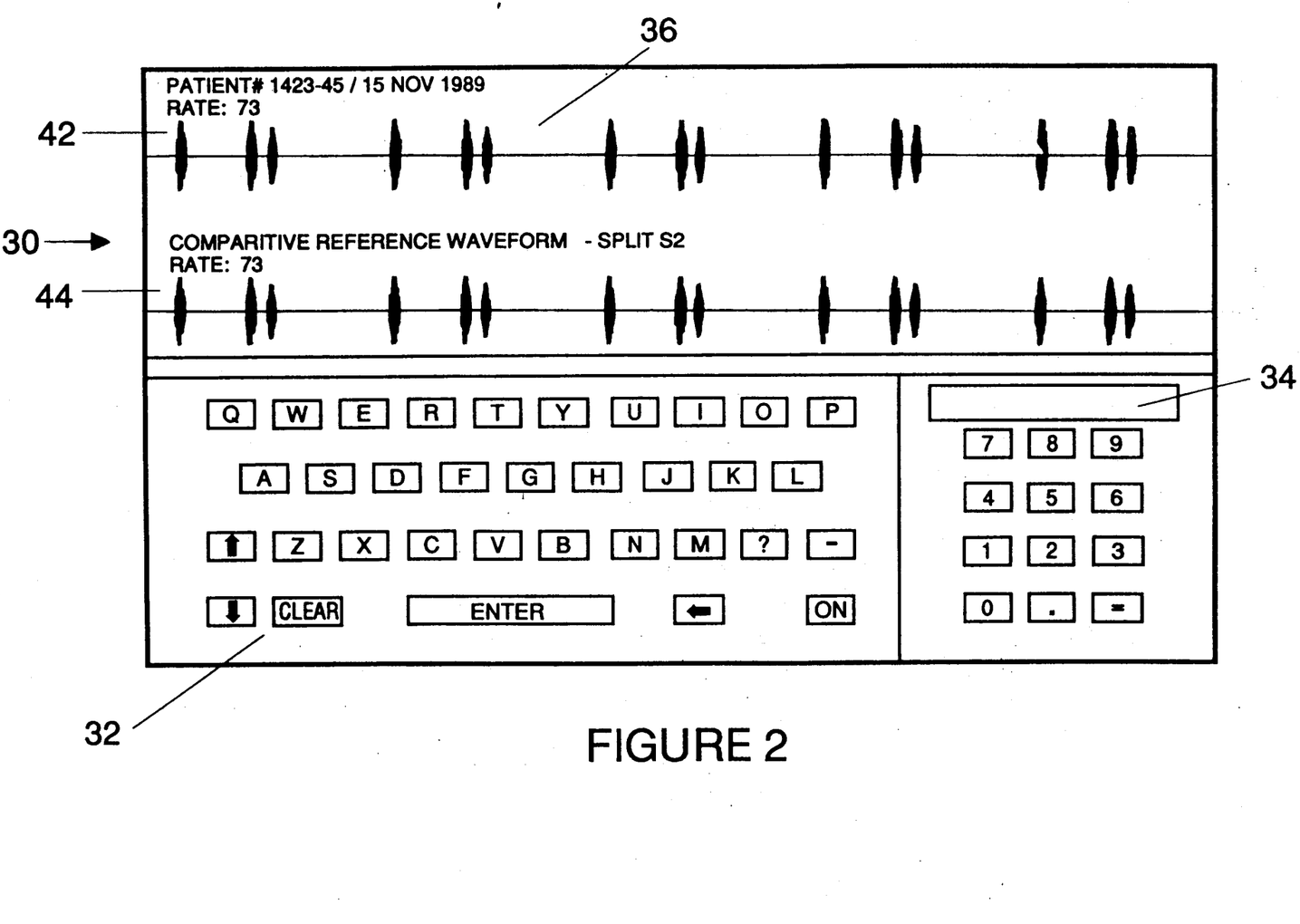
FIG. 2 is an illustration of a computer/display unit for use in accord with the present invention.

FIG. 2 illustrates a computer/display unit 30 for use with stethoscope 10. Recorded data is transmitted to computer/display unit 30 for further analysis. This computer/display unit may be either portable or may be a PC or other large computer. Computer/display unit 30 includes keyboard 32 for inputting data and controlling instructions into the computer. Keyboard 32 may include a visual alphanumeric display window 34. Graphic display screen 36 provides a means for displaying one or more graphic illustrations of phonocardiographic heart sounds. In FIG. 2, a pre-recorded reference sound 42 is displayed in the upper half of screen 36 while the patient's sound 44 is displayed in the lower half. Additional information, such as patient identification, heartrate, identification of the reference sound and provisional identification of the patient's heart sounds may also be displayed as seen in FIG. 2.

Figure 3:
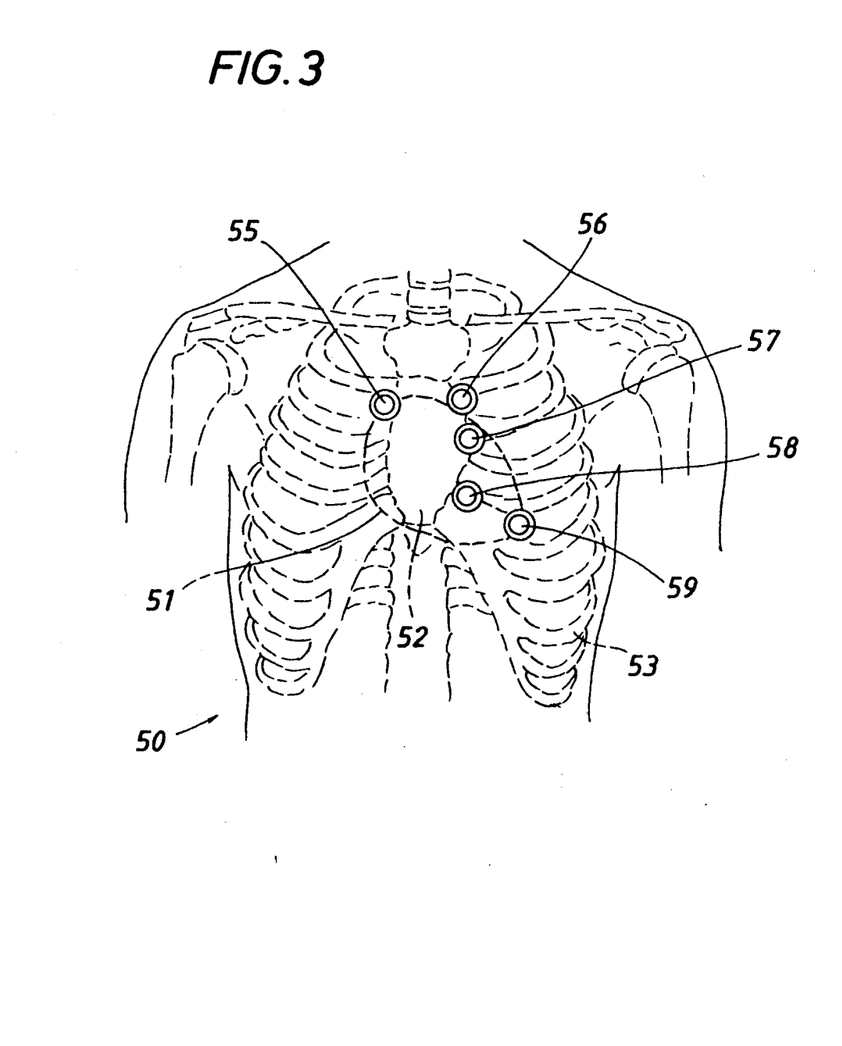
FIG. 3 is an illustration of five conventional locations in the human torso for detecting phonocardiographic heart sounds.

One of the variables which appears in the phonocardiographic signature and which is employed in analysis thereof is the location of the stethoscope cup during detection of the phonocardiographic heart sounds. Those skilled in the art are well aware of the conventional locations where these sounds are detected. FIG. 3 illustrates the most common locations. FIG. 3 provides a simple medical illustration of the chest cavity of a patient 50 illustrating the location of the heart 51, sternum 52 and ribs 53. The conventional listening areas are disclosed as the aortic area 55, the pulmonic area 56, the Erbs point 57, the tricuspid area 58 and the mitral area 59. In the method of the present invention each of these conventional areas, and any others chosen by the user, may be provided with a specific alpha or numeric identifier which is easily input using controls 28 for storage with the digital data.

Figure 4A:
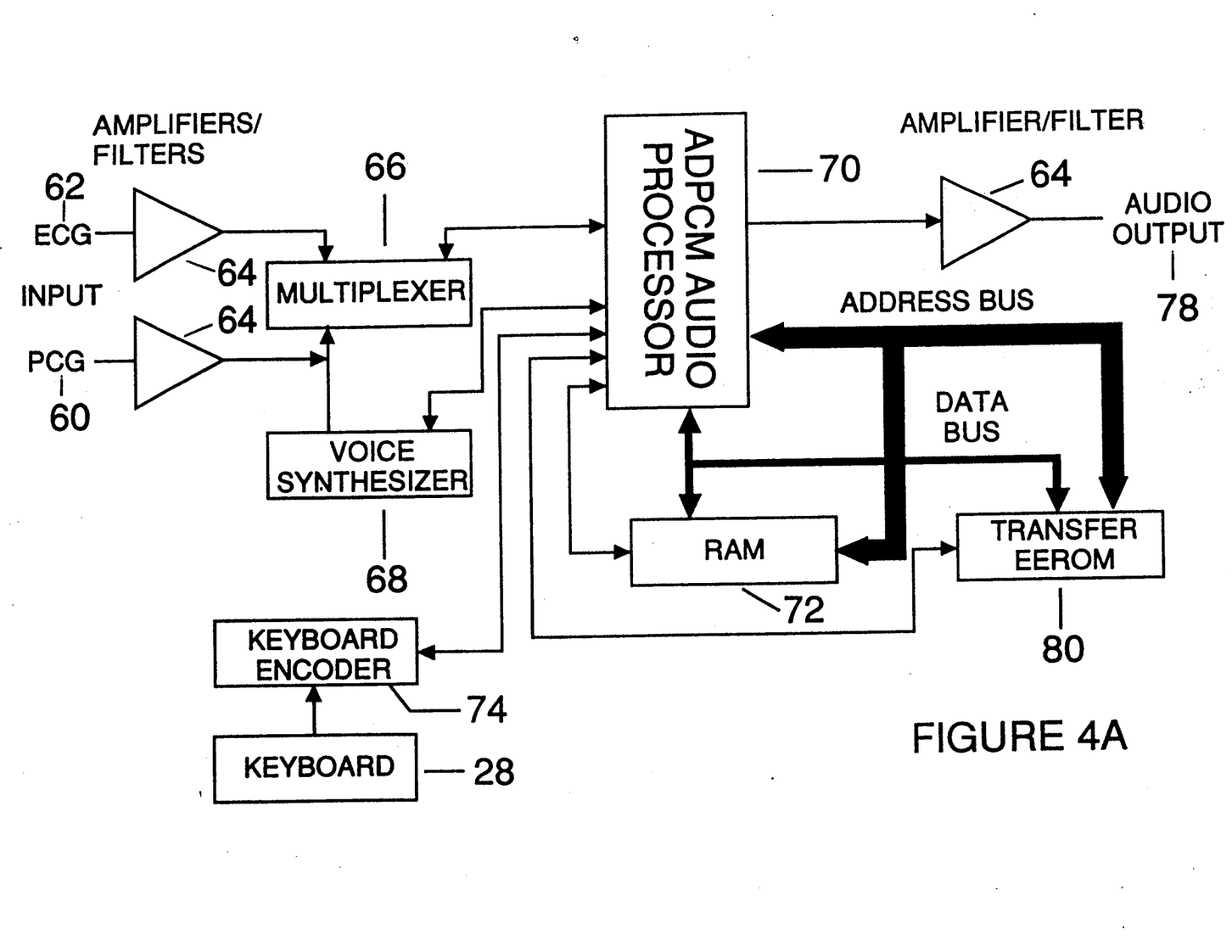
FIG. 4A is a schematic diagram of the main features of the electronic portion of a recording, digital stethoscope in accord with the present invention.
Figure 4B:
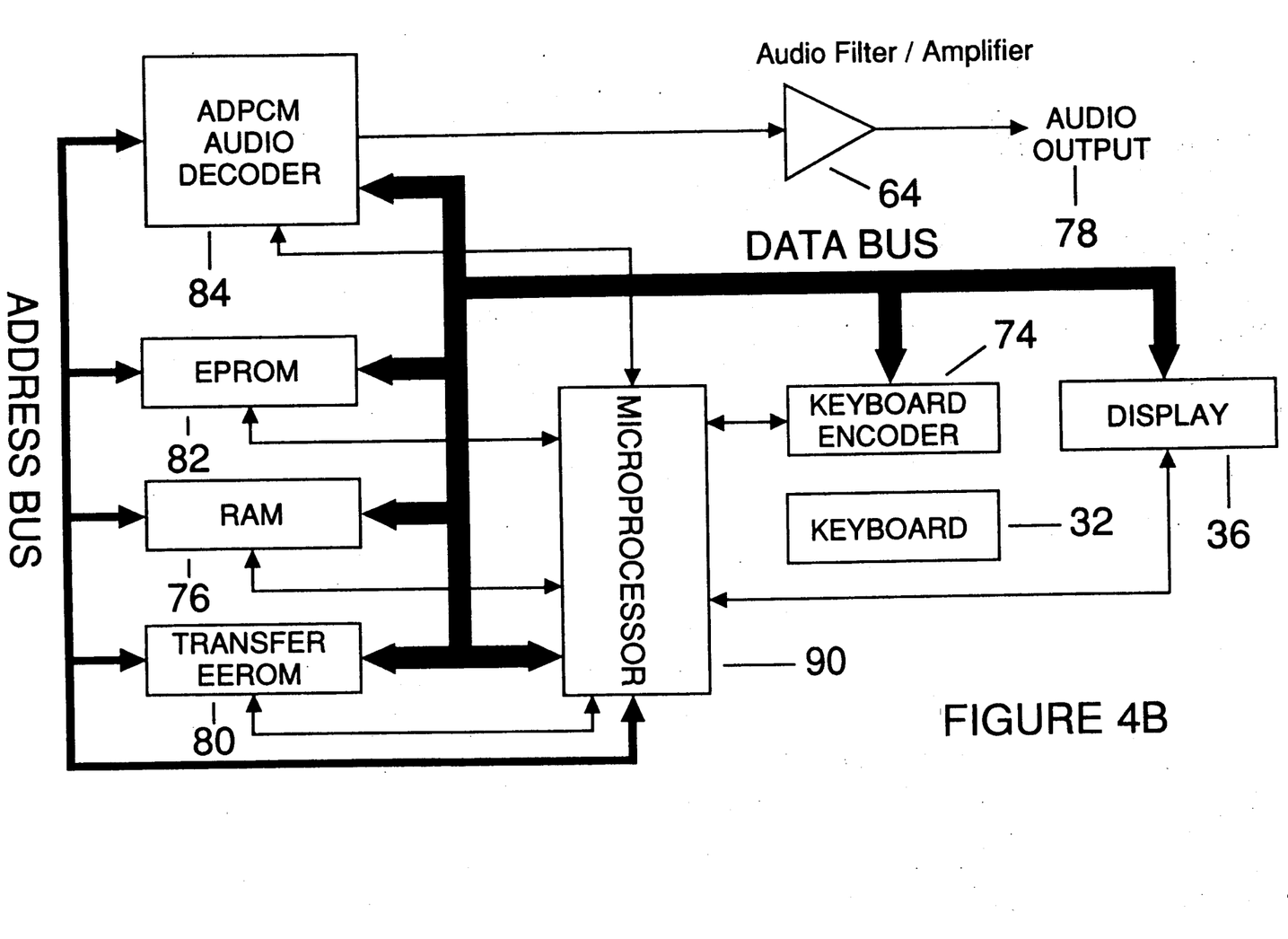
FIG. 4B is a schematic diagram of the main feature of the computer/display unit of the system of the present invention.

FIGS. 4A and 4B, respectively, illustrate the basic electronics of a recording digital stethoscope 10 and computer/display unit 30 in accord with the present invention. Those skilled in the art are aware that many other configurations and components might be used to accomplish the desired result. Stethoscope cup 12 detects the phonocardiographic sounds input to the recording, digital stethoscope at 60. Transducers 18 disposed about stethoscope cup 12 similarly detect the electrocardiographic wave pattern for input 62. Both signals are processed through conventional amplifier/filter circuits 64 for input to analog-to-digital processor 70 through multiplexer 66. Keyboard 28 and keyboard encoder 74 are employed to input additional identifying information into processor 70. In the illustrated embodiment minimal information is input through keys 28 on stethoscope 10. In an alternative embodiment, voice synthesizer 68 might be used to permit identifying information to be input through voice control. The signals digitalized in processor 70 are stored in the memory of RAM (Random Access Memory) 72. If desired, these digital sounds might then be replayed through appropriate amplifier/filter circuitry 64 and audio output 78. In stethoscope 10, audio output is through speaker 22. These digital signals are transmitted to transfer EEROM (Electrical Erasable Read Only Memory) 80 for transmission to a computer/display unit 30.

FIG. 4B illustrates schematically the basic components of the separate computer/display unit 30. In this unit digital data is received from transfer EEROM 80. The digitized PCG and ECG data signals together with any additional data, including the reference library, is stored in the memory of RAM (Random Access Memory) 76. Processing and analysis of the digital data is handled in microprocessor 90. Additional identifying data and controlling instructions may be provided to microprocessor 90 through keyboard 32 and keyboard encoder 74. Programmed instructions may be stored in EEROM 82. Again, audio output of the recorded phonocardiographic heart sounds of the patient or of the reference sounds may be output by processing through digital-to-analog audio decoder 84 and appropriate amplifier/filter circuits 64 to audio output 78. Alternatively, the phonocardiographic heart sounds may be visually displayed using visual display screen 36.

Figure 5A:
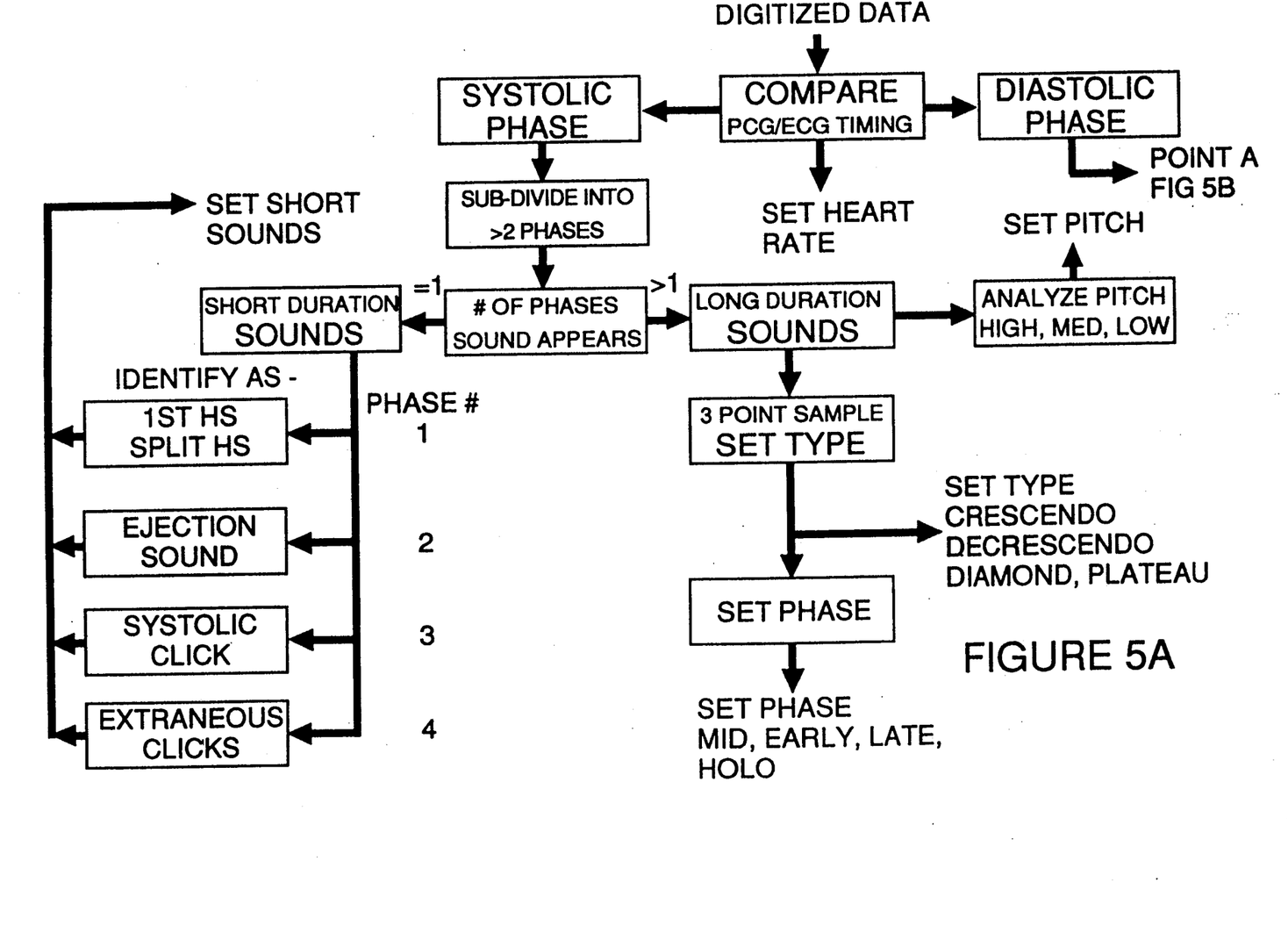
FIGS. 5A, 5B and 5C are a flow diagram illustrating a preferred method of analyzing the digitalized phonocardiographic data in accord with the present invention.
Figure 5B:
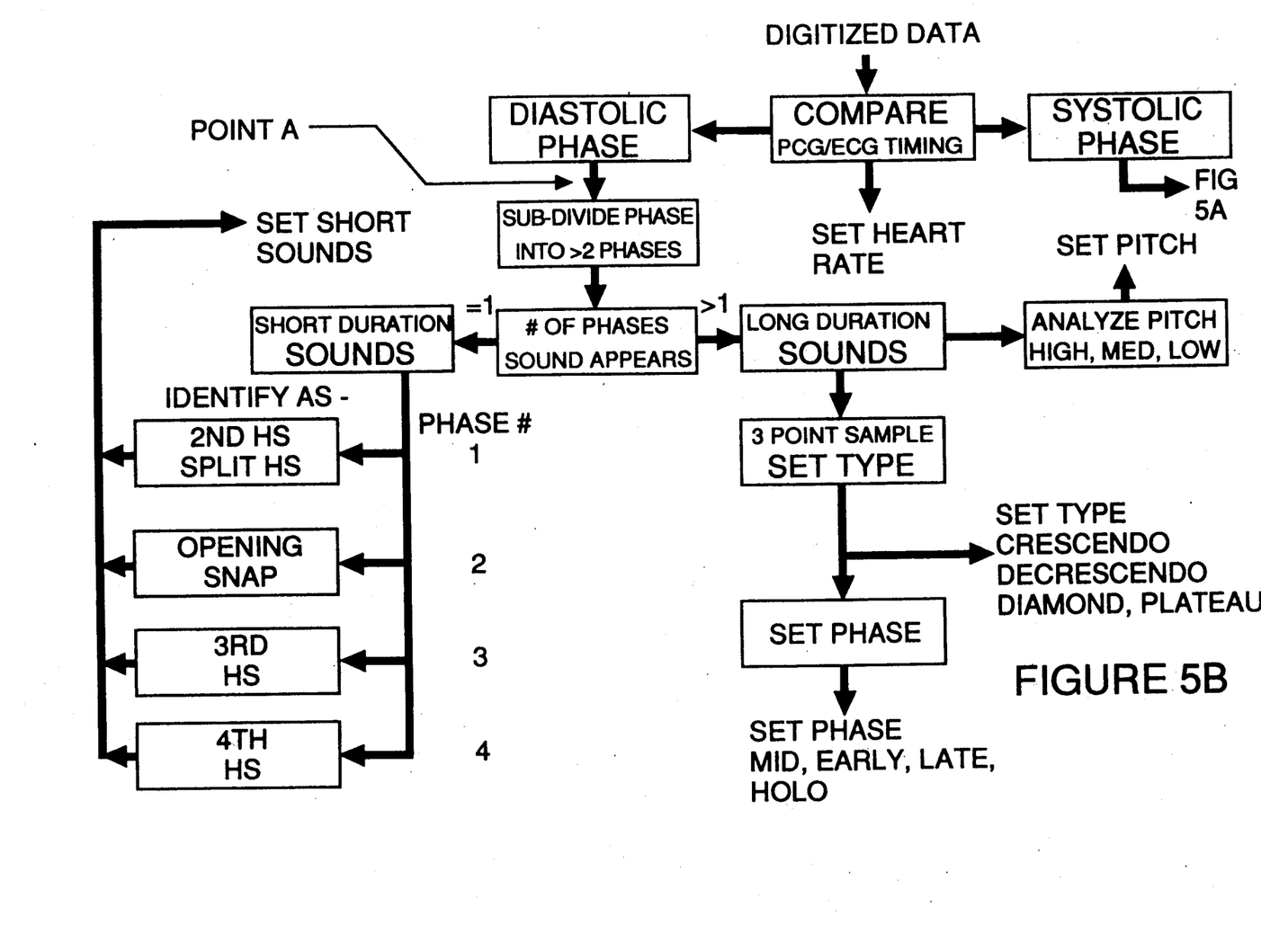
Figure 5C:
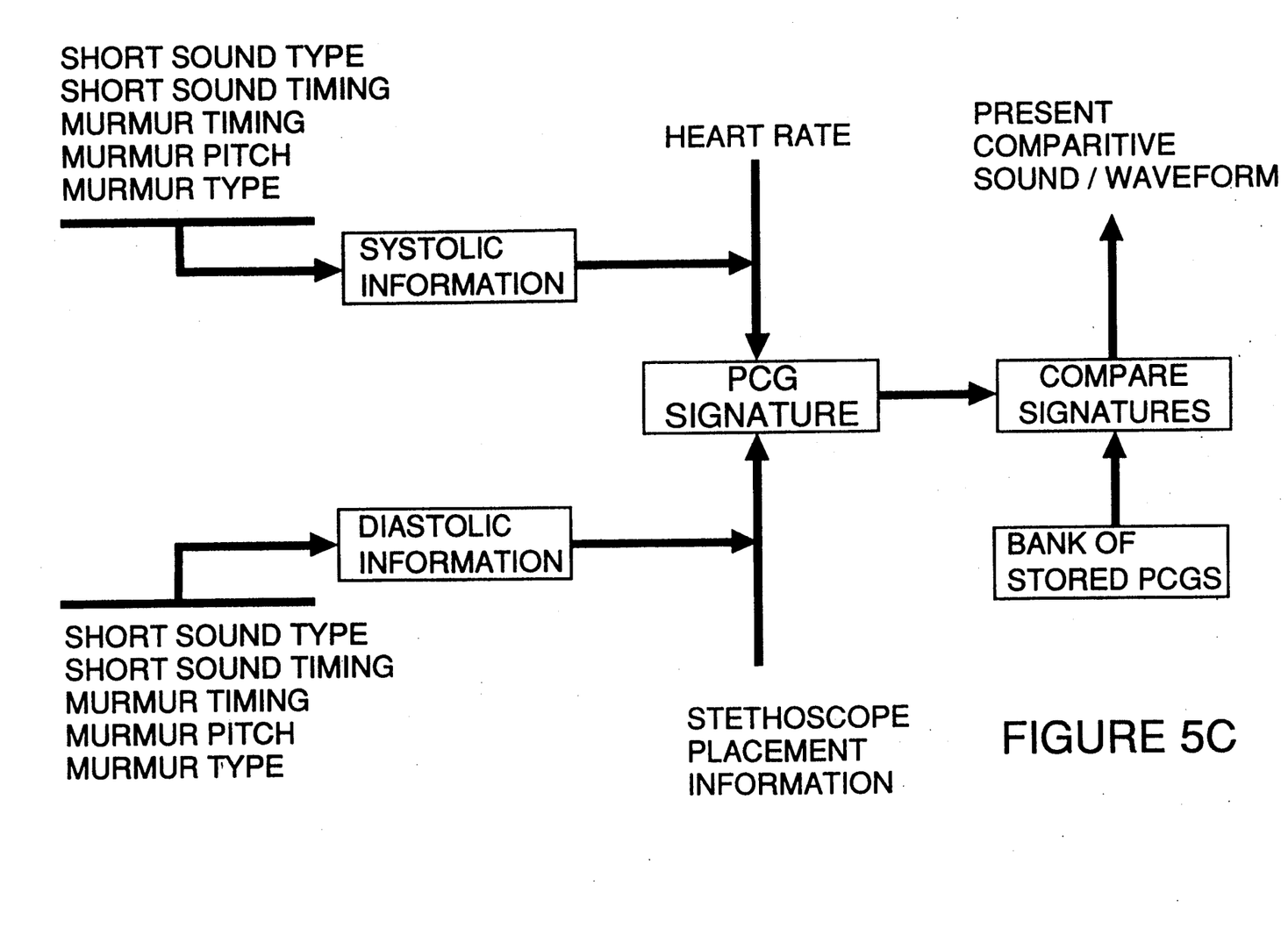

FIGS. 5A, 5B and 5C provide a simple flow diagram illustrating the preferred method of analyzing the digitalized phonocardiographic sounds to produce a phonocardiographic signature for the patient. The heart rate is determined from the R-wave of the electrocardiographic wave pattern and stored. From the electrocardiographic signal the systolic and diastolic phases of the heartbeat are determined. By comparing the ECG and PCG signals the systolic and diastolic phases of the phonocardiographic signals may be determined.

FIG. 5A illustrates analysis of the heart sounds in the systolic phase. The systolic phase is divided into at least two, and, preferably four, subphases. The sounds appearing in each of these subphases are then analyzed. Sounds occurring in a single subphase are identified as short duration heart sounds. These sounds may be the first and second heart sounds and splitting of these sounds, the third and fourth heart sounds, clicks and ejections sounds. Each short sound is identified by the phase and subphase in which it appears together with its timing with reference to the R-wave. The identification of each short sound is stored within the memory. Long duration heart sounds are those sounds which occur in more than one adjacent subphase. Long duration heart sounds are generally known as murmurs. Each long duration heart sound is further analyzed for pitch. Pitch may be simply identified as low, medium or high with appropriate frequency divisions chosen by the user. The location of each long duration sound is also established by reference to the subphases in which it occurs. For example, location may be identified and set as early, mid, late or holo. Finally, each long duration heart sound is further analyzed for type, i.e., shape. Shapes are identified as crescendo (high back with increasing leading edge), decrescendo (high front with decreasing trailing edge), diamond (high middle with increasing leading edge and decreasing trailing edge) and plateau (abrupt front and back with relatively constant middle). Detection of the amplitude of a long duration heart sound at three appropriately spaced intervals provides an easy means of determining the shape. Comparison of three amplitudes so determined easily permits the long sound to be classified into one of the above classifications. Once identified, the shape of each long duration sound is stored in the memory together with the previously identified phase, location and pitch.

FIG. 5B illustrates a similar analysis pattern for the sounds in the diastolic phase.

FIG. 5C illustrates final determination of the phonocardiographic signature for the patient. The patient's phonocardiographic signature is comprised of the systolic PCG signature as determined above, the diastolic signature as determined above, the heart rate and the location of the stethoscope during data acquisition. The PCG signature thus created provides a unique set of characteristics identified with the patient's specific phonocardiographic heart sounds. This PCG signature is readily compared with PCG signatures stored in a reference library within the computer to select one or more reference PCG signatures exhibiting features similar to those of the patient's signature. This method permits initial analysis to be based on strictly objective variables determined and assigned in developing the PCG signature. Criterion for electing reference PCG signatures similar to the determined patient signature are easily established. For example, each reference PCG signature having in common a predetermined number of variables with the PCG signature of the patient may be selected. These criteria are easily established and altered as desired by the user. This system minimizes the specialized knowledge required by the user. Further, this system eliminates many of the subjective and variable aspects of phonocardiographic analysis. However, it is not believed that all such variables should be eliminated and, accordingly, the method and system merely provides a means for selecting from the full library of recorded PCG signatures one or more signatures for final visual and/or audio display and comparison with the patient's heart sounds. Accordingly, the physician can make a final diagnosis from visual and/or audio analysis of the patient's recorded phonocardiographic heart sounds with those of the heart sounds selected by the system from the reference library as most likely matches.

The foregoing description of the invention has been directed in primary part to a particular preferred embodiment in accordance with the requirements of the patent statutes and for purposes of explanation and illustration. It will be apparent, however, to those skilled in the art that many modifications and changes in the specifically described apparatus may be made without departing from the scope and spirit of the invention. For example, the recording, digital stethoscope may provide the capability of detecting and recording a more complete electrocardiographic wave pattern than that described. Alternatively, the phonocardiographic signature may include other variables than those described herein. Therefore, the invention is not restricted to the particular form of construction and method illustrated and described, but covers all modifications which may fall within the scope of the following claims.

It is applicant's intention in the following claims to cover such modifications and variations as fall within the true spirit and scope of the invention.

We claim:

1. A method for identifying characteristic phonocardiographic sounds, comprising:
    detecting the phonocardiographic (PCG) sounds of a patient during both the systolic and diastolic phases of the heart beat;
    detecting simultaneously at least a portion of the electrocardiographic (ECG) wave pattern of said patient;
    converting both the detected PCG sounds and ECG wave pattern for the patient to digital electrical signals;
    storing said digital electrical signals representing said PCG sounds and ECG wave pattern of said patient in a memory means;
    inputting the location of the stethoscope where said PCG sounds were recorded;
    transmitting said stored digital signals to a digital computer; and
    analyzing said stored digital PCG signals in said computer to produce a PCG signature for said patient, said PCG signature comprising a plurality of characteristics selected from the heart rate of said patient, said location, the type and timing of each short heart sound in said systolic phase, the pitch, type and timing of each long heart sound in said systolic phase, the type and timing of each short heart sound in said diastolic phase and the pitch, type and timing of each long heart sound in said diastolic phase.

2. The method of claim 1 further comprising comparing said PCG signature of said patient with reference PCG signatures of reference heart sounds wherein said reference PCG signatures and the corresponding reference heart sounds from which they were derived are stored, respectively, in a plurality of database storage locations in said digital computer.

3. The method of claim 2 further comprising selecting from said stored reference PCG signatures one or more reference PCG signatures which resemble said PCG signature of said patient; and
    displaying said PCG heart sounds of said patient in juxtaposition with said reference heart sounds corresponding to at least one of said selected reference PCG signatures.

4. The method of claim 3 wherein said displaying comprises producing a visual representation of said patient PCG heart sounds and said reference heart sounds corresponding to at least one of said selected reference PCG signatures.

5. The method of claim 3 wherein said displaying comprises producing an audio signal of said patient PCG heart sounds and said reference heart sounds corresponding to at least one of said selected reference PCG signatures using a speaker and associated electronic circuitry.

6. The method of claim 1 wherein said analysis includes the steps of:
    recording the location of the stethoscope where said PCG sounds and said ECG wave pattern were detected;
    determining the heart rate of said patient from said ECG wave pattern;
    dividing the PCG measurement of said patient into a systolic phase and a diastolic phase;
    dividing said systolic phase and said diastolic phase each into at least two subphases;
    identifying each sound in said PCG measurement of said patient as a short sound or a long sound by determining whether each said sound appears in one or in more than one subphase in each phase;
    identifiying each said short sound by the phase and subphase in which it appears and by its timing;
    identifying each said long sound by the phase and subphase in which it appears and by its pitch, shape and timing;
    producing a systolic PCG signature including the type and timing of each short sound and the pitch, type and timing of each long sound found in the systolic portion of said PCG sounds of said patient;
    producing a diastolic PCG signature including the type and timing of each short sound and the pitch, type and timing of each long sound found in the diastolic portion of said PCG sounds of said patient; and
    producing a PCG signature of said patient including said systolic PCG signature, said diastolic PCG signature, said heart rate and the location of said stethoscope when said PCG sounds and said ECG wave pattern were detected.

7. A system for identifying characteristic phonocardiographic (PCG) sounds, comprising;
    a recording, digital stethoscope comprising means for detecting the phonocardiographic (PCG) sounds and at least a portion of the electrocardiographic (ECG) wave pattern of a patient including the systolic and diastolic portions, means for converting said detected PCG sounds and said ECG wave pattern to digital electrical signals, and means for recording said digital signals within said stethoscope;

means for transmitting the recorded digital signals to a computer;

said computer including memory means for storing a library of reference PCG signatures together with the corresponding reference heart sounds from which they were derived, and for receiving and storing the PCG signals of said patient from said recording, digital stethoscope, and computing means for producing a PCG signature of said patient from said PCG sounds and ECG wave pattern of said patient and for comparing the PCG signature of said patient with PCG signatures in said reference library for selecting one or more reference PCG signatures closely matching said PCG signature of said patient; and means for displaying in juxtaposition said PCG heart sounds of said patient and said reference heart sounds corresponding to at least one of said selected reference PCG signatures.

8. A recording, digital stethoscope, comprising:
first means for detecting phonocardiographic (PCG) heart sounds;
means for converting said detected PCG sounds into digital PCG signals;
second means for simultaneously detecting at least a portion of the electrocardiographic (ECG) wave pattern;
means for converting said detected ECG wave pattern into digital ECG signals; and
memory means within said stethoscope having a plurality of first storage locations for storing said digital PCG signals and a plurality of second storage locations for storing said digital ECG signals.

9. The digital stethoscope of claim 8 wherein said second detecting means detects the portions of said ECG wave pattern associated with the systolic and the diastolic portions of the heart beat.

10. The digital stethoscope of claim 8 wherein said detected portion of said ECG wave pattern is the R-wave.

11. The digital stethoscope of claim 8 wherein said ECG detecting means comprises at least three electrodes disposed about the periphery of said stethoscope cup.

12. The digital stethoscope of claim 11 wherein said electrodes are symmetrically disposed.

13. The digital stethoscope of claim 8 further comprising a speaker and playback circuitry for producing an audio output using said digital PCG signals.

14. The digital stethoscope of claim 8 further comprising means for recording the location of said stethoscope when said PCG sounds and said ECG wave pattern were recorded.

15. The digital stethoscope of claim 8 further comprising means for conveying said detected PCG sounds to the ears of a user of said stethoscope.

16. A recording, digital stethoscope, comprising:
first means for detecting phonocardiographic (PCG) heart sounds;
means for conveying said detected PCG sounds to the ears of a user of said stethoscope;
means for converting said detected PCG sounds into digital PCG signals; and
memory means having a plurality of first storage locations for storing said digital PCG signals within said stethoscope.

17. The stethoscope of claim 16 wherein said detecting means comprises a stethoscope cup and said conveying means comprises an air column in a flexible tube adapted at a first end with ear pieces and affixed at a second end to said stethoscope cup.

18. The stethoscope of claim 17 further comprising means for variably amplifying said detected PCG sounds in said air column.

19. The stethoscope of claim 18 wherein said variable amplifying means comprises an analog amplifier.

20. The stethoscope of claim 16 wherein said means for converting comprises a transducer for converting said detected PCG sounds into analog electrical signals and an analog to digital converter.

21. The stethoscope of claim 16 further comprising a speaker and playback circuitry for producing an audio output using said digital PCG signals.

* * * * *